United States Patent [19]

Osipow et al.

[11] Patent Number: 5,180,753
[45] Date of Patent: Jan. 19, 1993

[54] PROCESS FOR THE MANUFACTURE OF SYNTHETIC POLYMER PROPELLANT SYSTEMS

[76] Inventors: Lloyd I. Osipow, 2 Fifth Ave., New York, N.Y. 10011; Dorothea C. Marra, 107 Fernwood Rd., Summit, N.J. 07901; J. George Spitzer, 44 Coconut Row, Palm Beach, Fla. 33480

[21] Appl. No.: 605,750

[22] Filed: Oct. 30, 1990

Related U.S. Application Data

[62] Division of Ser. No. 230,680, Aug. 8, 1988, Pat. No. 4,996,240, which is a division of Ser. No. 867,580, May 28, 1986, abandoned.

[51] Int. Cl.$^5$ .............................................. C08J 9/28
[52] U.S. Cl. ......................................... 521/65; 521/78; 521/79; 521/82; 521/88; 521/98; 521/910
[58] Field of Search ................... 521/910, 65, 78, 79, 521/82, 88, 98; 424/81

[56] References Cited

U.S. PATENT DOCUMENTS

| | | | |
|---|---|---|---|
| 3,912,667 | 10/1975 | Spitzer et al. | 521/98 X |
| 4,328,319 | 5/1982 | Osipow et al. | 521/98 X |
| 4,432,920 | 2/1984 | Ishikawa et al. | 521/65 X |

*Primary Examiner*—Joseph L. Schofer
*Assistant Examiner*—J. M. Reddick
*Attorney, Agent, or Firm*—Morgan & Finnegan

[57] ABSTRACT

Compositions and a process for manufacture are provided for synthetic polymer-propellant systems that form cohesive foamed structures from which aqueous solutions can be expressed, where the useful temperature range over which these structures form is broadened by using a propellant mixture consisting predominantly of a propellant that is a poor solvent for the polymer and has a vapor pressure in the range of 10–35 psig at 20 C in combination with a small amount of a propellant that is a good solvent for the polymer; and where these coherent foamed structures can be formed even with aqueous solutions containing 0 to about 30% alcohol, provided that insoluble fine-particle solids that do not pack and become difficult to redisperse are included in the composition.

2 Claims, No Drawings

PROCESS FOR THE MANUFACTURE OF SYNTHETIC POLYMER PROPELLANT SYSTEMS

This is a divisional of co-pending application Ser. No. 07/230,680 filed Aug. 8, 1988, now U.S. Pat. No. 4,996,240, which is a FWC Divisional application of U.S. Ser. No. 06/867,580 filed May 28, 1986, now abandoned.

BACKGROUND OF THE INVENTION

This invention is concerned with polymer-propellant compositions that are capable of forming foamed structures containing open and/or closed cells from which an aqueous solution can be expressed. Similar compositions have been described by Spitzer et al U.S. Pat. Nos. 3,912,665,-6,-7, patented Oct. 14, 1975. These earlier compositions suffered preparation and the narrow temperature range over which coherent foamed structures could be obtained.

A practical procedure for preparing polymer-propellant compositions that are capable of forming foamed structures containing open end/or closed cells is described by Osipow, et al in U.S. Pat. No. 4,328,319. This process comprised coating the synthetic polymer in particulate form with an inert solid material insoluble in the propellant.

Spitzer, et al in U.S. Pat. No. 4,422,877 described synthetic polymer-liquified propellant compositions capable of forming a cold foamed structure having a temperature at least 30 C. below the ambient temperature at which the cold foamed structure is formed, which contain from 50 to 90% be weight of propellant having a heat of vaporization of at least 55 calories per gram, and at least one liquified propellant boiling below −10 C.

OBJECTS OF THE INVENTION

This invention is concerned with pressurized compositions consisting of a polymer dissolved in a liquified propellant mixture emulsified with an aqueous solution containing from zero to about 60% alcohol, which forms upon release from its container a coherent foamed structure from which the aqueous solution can be expressed. Previously, such coherent foamed structures would form only over a relatively narrow temperature, e.g., 18°-26° C. At lower temperatures the structures tended to be excessively weak, while at higher temperatures they tended to form ribbons rather than coherent pads. An object of the instant invention is to provide compositions that form coherent foamed pads over a broader ambient temperature range, and at least over the range of 15°-32° C.

Previously, such emulsions containing less than about 30% alcohol based on the weight of the aqueous-phase could not be used to form coherent foamed structures from which the aqueous solution could be expressed. Instead, an aqueous foam containing polymer shreds was obtained If the amount of aqueous solution was reduced sufficiently, then a coherent foamed structure was obtained, but it was dry and the aqueous solution could not be squeezed out. An object of the invention is to provide compositions that form coherent structures from which aqueous solutions containing from 0 to 60% alcohol can be expressed.

Previously, an inexpensive, rapid and convenient process for the manufacture of pressurized compositions that form coherent foamed structures and from which an aqueous solution could be expressed was not available. It is an object of this invention to provide such a process.

NATURE OF THE INVENTION

It has now been found that the objects of the instant invention can be realized using polyisobutyl methacrylate as the polymer of the polymer - propellant composition. The molecular weight of the polymer is not critical and it can range from 25,000 to about 500,000. The composition should contain from about 5 to about 40% by weight of polymer. The lower concentration levels are employed with higher molecular weight polymers and the higher concentration levels with polymers of lower molecular weight. If the concentration is too low the foamed structure will be excessively weak, while if it is too high, the polymer solution will be too viscous to mix readily with the aqueous phase.

It is necessary to plasticize the polymer, both to obtain a coherent foamed structure and to obtain a pad structure that is soft and flexible, rather than harsh and brittle. However, it is important not to over-plasticize, otherwise the structure will be weak and it will stretch excessively during use. If still more over-plasticized, it will be a sticky paste rather than a foamed structure.

Any of the wide variety of plasticizers may be used, as shown in the prior art. It is preferable, however, to use a plasticizer that only exerts a mild plasticizing effect, so that small variations in dosing will not substantially change the character of the product. Vegetable oils meet this requirement. The propellants also act as fugitive plasticizers, since they do not evaporate completely within the seconds that elapse between the time that the foamed structure is formed and it is used.

The choice of propellant plays an important role in extending the temperature range over which cohesive foamed structures can be obtained. In accordance with the instant invention, the propellant should be a mixture of propellants consisting predominantly of propellants that are poor solvents for the polymer and have relatively low vapor pressures, i.e. about 10 to 35 psig at 20 C. These propellants should comprise from about 50 to about 98% of the propellant mixture by weight and should be selected from the group consisting of n-butane, isobutane, and 1, 2-dichlorotetrafluoroethane. The use of these propellants to a predominant extent, and in particular n-butane and 1, 2-dichlorotetrafluoroethane, extends the upper temperature range at which coherent foamed structures are obtained.

It has now been found that the second component of the propellant mixture should be a propellant that is a good solvent for the polymer and should be selected from the group consisting of dimethyl ether and 1-chloro-1,1 difluoroethane. These propellants should comprise from about 2 to about 25% by weight of the propellant mixture. Combinations of these good solvent propellants as well as combinations of the relatively low vapor pressure propellants may be used.

In the absence of these good solvent propellants, at cold ambient temperatures the polymer-propellant solution forms a coacervate consisting of a polymer-rich phase and a polymer-poor phase. The polymer-rich phase tends to be too viscous and a coherent foamed structure does not form. The good solvent tends to prevent the formation of a coacervate and thus it extends the lower temperature range at which coherent foamed structures form.

In addition to these essential propellants, other liquified propellants may be used These include n-propane, dichlorodifluoromethane, and 1, 1 difluoroethane. The propellant mixture comprises from 20 to 60% by weight of the composition.

The second liquid phase of the composition is an aqueous phase-containing emulsifying agents and active ingredients which may include deodorants, antiperspirants, bactericides, fungicides, antibiotics, moisturizers, keratolytic agents, etc. Until now, it has been necessary to use an aqueous solution containing at least about 30% of an alcohol, such as ethanol or isopropanol, in order to obtain a coherent foamed structure from which the aqueous solution could be expressed. In some instances, it has been possible to replace part of the alcohol by a glycol-ether, such as dipropylene glycol methyl ether. In the absence of this large amount of alcohol, an aqueous foam formed. It appears likely that the alcohol serves as an anti-foam, to repress the foaming of the aqueous phase and enables a coherent foamed structure to form.

It has now been discovered that various fine-particle solids that are not soluble in the composition can be used instead of all or part of the alcohol to enable coherent structures to form. Thus, the aqueous solution may contain from 0 to about 30% by weight of water-soluble alcohol, provided these fine-particle materials are present. With higher concentrations of alcohol, i.e., 30 to 60% of the aqueous solution by weight, these fine-particle solids are not essential. It is also necessary that the powder not pack during storage and become difficult to redisperse. The materials that have been found to be suitable are selected from the group comprising colloidal silica, bentonites, aluminum pigment and the soaps of fatty acids containing about 9 to 22 carbon atoms and di- and poly-valent cations, in particular, the stearates and palmitates of aluminum, calcium, magnesium and zinc.

Generally, from about 0.03 to about 3%, and preferably from about 0.1 to about 1%, of fine-particle solids are used, based on the weight of the composition. If the concentration is too low, it is ineffective, while higher concentrations reduce the cohesiveness of the foamed structure.

Employing the propellants and fine particle solids of the instant invention, as required, a surprisingly convenient process for the manufacture of these pressurized compositions has been discovered. A concentrate is prepared that is a dispersion of polyisobutyl methacrylate in water. The dispersion may include all of the ingredients except the propellant mixture and those ingredients that will adversely affect the stability of the dispersion. The latter are combined into a second concentrate. The dispersion may be a polyisobutyl methacrylate latex to which compatible ingredients have been added.

The concentrates are dosed into aerosol containers in the conventional manner. The propellant mixture is added, either through the valve or under the valve mounting cup, as is customary. It is then necessary to shake the containers for a few seconds, i.e., 5 to 30 seconds. The containers may be shaken while on the line, either before or after passing through the water-bath test, or they may be packed into cases and then shaken. The shaking action brings the dispersed polyisobutyl methacrylate particles into contact with the propellant mixture and they dissolve almost instantaneously, completing the manufacturing process.

The compositions of the instant invention consist essentially of the following in parts by weight of the total composition:

| | |
|---|---|
| Polyisobutyl methacrylate | 5–40% |
| Aqueous solution | 25–60% |
| Propellant | 20–60% | provided that from about 50 to 98% of the propellant mixture by weight consists of propellants that are poor solvents for the polymer and have vapor pressures in the range of 10 to 35 psig at 20 C. Such propellants are selected from the group consisting of n-butane, isobutane and 1, 2- dichlorotetrafluoroethane, and from about 2 to about 25% of the propellant mixture by weight is selected from the group consisting of dimethyl ether and 1-chloro-1, 1 difluoroethane, for the purpose of extending the temperature range over which coherent foamed structures are obtained; and where the aqueous solution contains less than about 30% alcohol, the composition also contains from about 0.03 to about 3.0% by weight of insoluble fine-particle solids selected from the group consisting of colloidal silica, bentonite, aluminum pigment and the soaps of fatty acids containing 9-22 carbon atoms and di- and polyvalent cations, for the purpose of insuring that a coherent foamed structure will form.

In place of polyisobutyl methacrylate other various acrylic and methacrylic copolymers having similar characteristics, including solubility in the propellant may be used in the instant invention. Examples of such copolymers are normal butyl methacrylate, copolymers of ethyl methacrylate and dodecyl methacrylate, etc.

The coherent foamed structures that are produced in accordance with the instant invention may be used as cleansing pads for cleaning parts of the body or for cleaning various surfaces Alternatively, they may be used as applicator pads that deliver aqueous solutions as well as oils along with the aqueous solution. Thus, they may be used to apply medicinal agents, lubricants, furniture polishes, etc.

The foamed structured pads of the present invention may be used for the same purpose of those of U.S. Pat. No. 4,328,319. See, for example, column 11, line 38 through column 15, line 40 of the aforementioned patent.

EXAMPLE 1

This example illustrates an astringent facial cleansing pad that exudes an aqueous solution containing 50% alcohol by weight. The composition forms coherent foamed structures over the temperature range 15 C. to 32 C.

| | Parts By Weight |
|---|---|
| Part 1 | |
| Sodium lauryl sarcosinate | 0.1 |
| Magnesium stearate | 0.3 |
| Ethanol | 25.7 |
| Water | 25.7 |
| Polyisobutyl methacrylate | 17.4 |
| Part 2 | |
| Polyoxypropylene(10)cetyl ether | 0.5 |
| Corn oil | 0.9 |
| Mineral oil | 1.5 |
| Part 3 | |
| Isobutane | 16.7 |
| n-Butane | 10.0 |

-continued

|  | Parts By Weight |
| --- | --- |
| 1. Chloro-1, 1 difluoroethane | 1.2 |

The components of Part 1 are combined to form a slurry of the polymer and the magnesium stearate in the hydro-alcohol solution. The components of Part 2 are combined to form an oil solution, and the components of Part 3 are combined to form a propellant mixture. Part 1 and Part 2 are separately dosed into aerosol cans, the valves are crimped on, and the propellant mixture is added through the valve. The cans are then shaken on the line for 10 seconds to dissolve the polymer.

EXAMPLE 2

This example illustrates a lathering scrub pad. It is used with water like a wash cloth impregnated with soap. The scrub pad lathers and cleans well. The hydro-alcohol solution used in the composition contains 33% alcohol. The composition forms coherent foamed structures over the temperature range 15 C to 32 C.

|  | Parts By Weight |
| --- | --- |
| Part 1 | |
| Sodium lauryl sarcosinate | 3.3 |
| Magnesium stearate | 0.3 |
| Witch Hazel | 13.3 |
| Ethanol | 16.8 |
| Water | 21.6 |
| Polyisobutyl methacrylate | 15.0 |
| Part 2 | |
| Polyoxypropylene(10)cetyl ether | 0.5 |
| Corn oil | 1.0 |
| Mineral oil | 1.6 |
| Part 3 | |
| Isobutane | 15.8 |
| n-Butane | 8.6 |
| 1, Chloro-1, 1 difluoroethane | 1.7 |

The procedure is the same as for Example 1, except that after adding the propellant, the cans are tested for leakage by passing through a water bath at 130F. They are then packed into cases and the cases are shaken for 30 seconds to dissolve the polymer.

EXAMPLE 3

This example illustrates a facial cleanser-freshener pad that cools as well as cleanses the face. The hydro-alcohol solution used in the composition contains 34% alcohol. The composition forms coherent foamed structures over the temperature range 15 C. to 32 C.

|  | Parts By Weight |
| --- | --- |
| Part 1 | |
| Pluronic L 121* | 0.2 |
| Zinc stearate | 0.3 |
| Witch Hazel | 10.0 |
| Ethanol | 11.6 |
| Water | 15.0 |
| Polyisobutyl methacrylate | 14.7 |
| Part 2 | |
| Corn oil | 1.3 |
| Mineral oil | 1.4 |
| Part 3 | |
| 1, 2 Dichlorotetrafluoroethane | 38.6 |
| 1, Chloro-1, 1 difluoroethane | 6.9 |

*Block copolymer of propylene oxide and ethylene oxide

The procedure is the same as for Example 1.

EXAMPLE 4

This example illustrates a vaginal and anal deodorant-cleansing wipe. The composition does not contain any alcohol to avoid any tendency for smarting. The composition forms coherent foamed structures over the temperature range 15 C. to 32 C.

|  | Parts By Weight |
| --- | --- |
| Part 1 | |
| Chlorohexidene gluconate | 0.4 |
| Pluronic L 72* | 0.2 |
| Colloidal silica | 0.4 |
| Water | 38.3 |
| Polyisobutyl methacrylate | 19.3 |
| Part 2 | |
| Corn oil | 2.5 |
| Mineral oil | 2.5 |
| Part 3 | |
| n, Butane | 32.2 |
| Dimethyl ether | 4.2 |

*Block copolymer of propylene oxide and ethylene oxide

The procedure is the same as for Example 2.

EXAMPLE 5

This example illustrates the use of a latex to form a composition suitable for use in the relief of acne. The pads have good cleansing action and leave a deposit that is keratolytic and antiseptic. The composition forms coherent foamed structures over the temperature range 15 C. to 32 C.

|  | Parts By Weight |
| --- | --- |
| Part 1 | |
| Polyisobutyl methacrylate latex (42%) solids | 49.1 |
| Colloidal silica | 0.4 |
| Part 2 | |
| Cetyl trimethyl ammonium bromide | 0.1 |
| Salicylic acid | 0.9 |
| Polyoxypropylene (10) cetyl ether | 1.9 |
| Tributyl citrate | 1.9 |
| Ethanol | 19.5 |
| Part 3 | |
| Isobutane | 12.4 |
| n-Butane | 11.5 |
| 1-Chloro-1,1-difluoroethane | 2.3 |

Separately, the ingredients of Part 1 and Part 2 are combined. Each of the two parts are dosed into aerosol cans, the valves are clinched on and the propellant mixture, Part 3, is added through the valve. The cans are then shaken on the line to dissolve the polymer.

EXAMPLE 6

This example illustrates a composition suitable for the treatment of cuts, scrapes, burns, etc. It is sufficiently cooling to provide relief from pain. It contains a stiptic to stop bleeding and an antiseptic. The level of alcohol is only 15% on the hydro-alcohol solution, so that it does not cause an alcohol sting. The composition forms coherent foamed structures over the temperature range 15 C. to 32 C.

|  | Parts By Weight |
| --- | --- |
| Part 1 | |
| Pluronic L121* | 0.2 |

-continued

| | Parts By Weight |
|---|---|
| Magnesium stearate | 0.4 |
| Cetyl trimethylammonium bromide | 0.1 |
| Aluminum chlorohydrate | 0.5 |
| Ethanol | 6.6 |
| Water | 36.3 |
| Polyisobutyl methacrylate | 21.8 |
| Part 2 | |
| Corn oil | 2.5 |
| Mineral oil | 2.0 |
| Part 3 | |
| n-Butane | 26.0 |
| Dimethyl ether | 3.6 |

*Block copolymer of propylene oxide and ethylene oxide

The procedure is the same as for Example 1.

We claim:

1. A process for the manufacture of a polymer-propellant composition that forms a coherent foamed structure from which an aqueous solution can be expressed consisting of about 5% to about 40% by weight of polymer selected from the group consisting of acrylic and methacrylic acid ester homopolymers and copolymers, from 25% to 60% by weight of an aqueous solution containing from 0 to 60% alcohol, from 20% to 60% by weight of propellant based on the weight of the composition, said process comprising dispersing the polymer in the aqueous solution and dosing said dispersion into a container prior to adding the propellant, adding the propellant to the container and subjecting the resulting composition in the container to a shaking action to bring the dispersed polymer particles into contact with the propellant thereby causing the polymer particles to dissolve quickly in the propellant.

2. A process for the manufacture if a polymer-propellant composition as in claim 1, where the polymer dispersed in aqueous solution is a latex.

* * * * *

UNITED STATES PATENT AND TRADEMARK OFFICE
CERTIFICATE OF CORRECTION

PATENT NO. : 5,180,753
DATED : January 19, 1993
INVENTOR(S) : Osipow et al

It is certified that error appears in the above-indentified patent and that said Letters Patent is hereby corrected as shown below:

Column 1, line 18, after "suffered" insert-- from a number of disadvantages including the difficulty of --.

Column 8, line 1, claim 2, "if" should read --of--.

Signed and Sealed this

Twenty-sixth Day of October, 1993

Attest:

BRUCE LEHMAN

Attesting Officer    Commissioner of Patents and Trademarks